(12) United States Patent
Werner et al.

(10) Patent No.: US 9,033,877 B2
(45) Date of Patent: May 19, 2015

(54) DEVICE AND METHOD FOR DETERMINING BLOOD GLUCOSE CHARACTERISTICS

(75) Inventors: Karl Werner, Wiesloch (DE); Peter Blasberg, Weinheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 389 days.

(21) Appl. No.: 13/032,672

(22) Filed: Feb. 23, 2011

(65) Prior Publication Data

US 2012/0215085 A1  Aug. 23, 2012

(51) Int. Cl.
*A61B 5/00* (2006.01)
*A61B 5/145* (2006.01)
*G06F 19/00* (2011.01)

(52) U.S. Cl.
CPC ........... *A61B 5/14532* (2013.01); *A61B 5/7275* (2013.01); *A61B 5/743* (2013.01); *G06F 19/3406* (2013.01)

(58) Field of Classification Search
CPC ........................ A61B 5/14532; G06F 19/3406
USPC .......................................... 600/345, 347, 365
See application file for complete search history.

(56) References Cited

U.S. PATENT DOCUMENTS

| | | | |
|---|---|---|---|
| 7,399,277 B2 | 7/2008 | Saidara et al. | |
| 8,279,226 B2 * | 10/2012 | Krieftewirth | 345/440.1 |
| 2002/0065453 A1 * | 5/2002 | Lesho et al. | 600/347 |
| 2004/0153257 A1 | 8/2004 | Munk | |
| 2006/0137695 A1 | 6/2006 | Hellwig et al. | |
| 2007/0066873 A1 | 3/2007 | Kamath et al. | |
| 2007/0255123 A1 | 11/2007 | Cummings et al. | |
| 2007/0293790 A1 | 12/2007 | Bainczyk et al. | |
| 2008/0021666 A1 | 1/2008 | Goode, Jr. et al. | |
| 2008/0234992 A1 | 9/2008 | Ray et al. | |
| 2008/0255438 A1 | 10/2008 | Saidara et al. | |
| 2008/0287755 A1 | 11/2008 | Sass et al. | |
| 2009/0043525 A1 | 2/2009 | Brauker et al. | |
| 2009/0054753 A1 | 2/2009 | Robinson et al. | |
| 2010/0141656 A1 | 6/2010 | Krieftewirth | |
| 2010/0261987 A1 | 10/2010 | Kamath et al. | |
| 2010/0331654 A1 * | 12/2010 | Jerdonek et al. | 600/365 |

OTHER PUBLICATIONS

Accu-Chek Instant DM User's Manual, Boehringer Mannheim, 1996, excerpts.
Gross et al., "Performance Evaluation of the MiniMed® Continuous Glucose Monitoring System During Patient Home Use", Diabetes Technology and Therapeutics, vol. 2 No. 1 (2000), pp. 49-62.

* cited by examiner

*Primary Examiner* — Michael D'Angelo
*Assistant Examiner* — Christian Jang
(74) *Attorney, Agent, or Firm* — Roche Diabetes Care, Inc.

(57) ABSTRACT

A device is provided for determining blood glucose characteristics including a display configured for presenting a graphical representation of a plurality of measurements of blood glucose values, wherein the graphical representation comprises a trend indicator indicating an approximate value trend in the sensed blood glucose value over a recent series of measurements, based on graphical segments having different graphical styles assigned to different ranges of sensed blood glucose values to indicate a transition from a first range to a second range of sensed blood glucose values. An associated method for operating a device for determining blood glucose characteristics is also provided.

8 Claims, 2 Drawing Sheets

DEVICE AND METHOD FOR DETERMINING BLOOD GLUCOSE CHARACTERISTICS

TECHNICAL FIELD OF THE INVENTION

The present invention relates to a device and associated method for determining blood glucose characteristics.

BACKGROUND

Technologies for such devices and methods are used in order to determine characteristics of patients' measured blood glucose values. The objective is to give the patient as well as the attending medical staff information which enables the patient to deal with his blood glucose values in an improved and appropriate manner.

For people suffering from diabetes, in particular Diabetes Mellitus, it is especially important for them to keep their blood glucose values constantly at a particular level. A precondition for this is knowledge of their blood glucose value which is therefore measured using a blood glucose measuring device set up for this purpose. Blood glucose measuring devices are known in various embodiments.

The international standard way of measuring blood glucose levels are in terms of a molar concentration, measured in mmol/L (millimoles per liter, or millimolar, abbreviated mM). In some countries, mass concentration is measured in mg/dl (milligrams per deciliter). Since the molecular weight of glucose $C_6H_{12}O_6$ is about 180 g/mol, for the measurement of glucose, the difference between the two scales is a factor of about 18, so that 1 mmol/L of glucose is approximately equivalent to 18 mg/dl.

If it is determined, on the basis of the measured values, that the blood glucose value has exceeded the recommended level, medicine is administered, for example by means of insulin injection or the oral administration of Metformin, an oral antidiabeticum. If the blood glucose values fall below the ideal or recommended level, sugar must be orally ingested, for example through food or drink. If the ideal level is exceeded for an extended period of time, there is the danger of serious health complications such as blindness, kidney damage, limbs having to be amputated or neuropathy. If the exceeding of the prescribed blood glucose level is for a short time only but considerable, this can lead to nausea, dizziness, sweating or even conditions of confusion. Thus, it is particularly important for a diabetic to know his blood glucose values at all times so that he is able to implement the appropriate measures to avoid the blood sugar values deviating from the ideal levels.

Blood glucose measuring devices with which the blood glucose values of diabetics can be measured is known. For example, see US 2007/0293790 A1, the disclosure of which is hereby incorporated herein by reference in its entirety. Other exemplary devices include those sold by the Applicant under the registered trade mark, ACCU-CHEK®, including the ACCU-CHEK® Compact Plus system and the ACCU-CHEK® Aviva system.

It is known that blood glucose measurements can be made according to a continuous measurement regime. Such measurements are also known as CGM measurements (Continuous Monitoring blood Glucose Measurement). In this process, the blood glucose values are measured continuously in a continuous time period such that, for example, the progress of the blood glucose value can be collected over an entire day. The analysis of the measured blood glucose values can provide for the determination of several day trends. In this way it is possible to determine blood glucose fluctuations dependent on the time of day. A disadvantage of the continuous blood glucose measurements is firstly, due to the continuous measurements, it can lead to high costs and secondly that it leads to discomfort for the diabetic whereby the latter is caused by the permanent wearing of a subcutaneous sensor. This can lead to infections at the point of entry, intolerance of the plaster or skin irritation which prevents the device being worn permanently or for a long period of time, for example several months. A continuous measurement of the blood glucose values is described, for example, in the document, Gross et al., "Performance Evaluation of the MiniMed Continuous Glucose Monitoring System During Patient Home Use", Diabetes Technology & Therapeutics, 2 (2000)49.

In connection with the continuous monitoring of blood glucose values, it has been proposed to perform a so-called trend analysis. See, for example, US 2008/0287755 A1, the disclosure of which is hereby incorporated herein by reference in its entirety. Trend analysis can enable the rate of change to be determined on the basis of two or more blood glucose value measurements. The period of continuously monitoring can be between about 5 and about 30 minutes. Measurement periods of less than about 10 minutes or more than about 30 minutes can be provided. Within the measurement period, the CGM measurement is performed once per second or once per minute whereby constant or variable cycle lengths can be provided. The known method proposes that the trend thus determined can be presented on a display as a directional arrow.

Furthermore, discontinuous or structured blood glucose measurements are known which are especially also known as SMBG measurements (Self-Monitoring Blood Glucose measurement) and are characterized by the fact that blood glucose values are determined at particular time intervals by means of individual measurements and/or series of measurements. In this way, it is possible, with the help of such blood glucose measurements, which are also known as structured blood glucose measurements, to measure blood glucose values in close proximity to particular events, for example in relation to meals. Disadvantages of structured blood glucose measurement can arise if events relevant for the blood glucose value of the diabetic occur between the measurement times so that they are undetectable. Procedures have been described whereby an individual blood glucose measurement in the scope of a discontinuous measurement is used to determine the time for a subsequent further individual measurement according to certain parameters. The parameters take into account patient and environmental conditions. See, for example, US 2009/0054753 A1, the disclosure of which is hereby incorporated herein by reference in its entirety.

It has also been proposed to graphically present measurement related information. Examples of such presentations can be found in US 2007/0066873 A1, US 2008/0021666 A1, US 2008/0255438 A1, US 2009/0043525 A1, and U.S. Pat. No. 7,399,277 B2, the disclosures of each of which are hereby incorporated herein by reference in their respective entireties.

It is the object of the invention to provide a device for determining blood glucose characteristics and a method with improved user handling.

SUMMARY

This object and others that will be appreciated by a person of ordinary skill in the art have been achieved according to the embodiments of the present invention disclosed herein. In one embodiment, the present invention comprises a device for determining blood glucose characteristics, comprising a sensor input capable of receiving a signal from a sensor, the signal being based on a sensed blood glucose value of a user, a memory configured for storing a plurality of measurements of the sensed blood glucose value of the user from the received signal from the sensor, a display configured for presenting a graphical representation of the plurality of measurements of the blood glucose characteristic value, and a controller configured for controlling the presentation of the graphical representation on the display, wherein the graphical representation comprises a trend indicator indicating an approximate value trend in the sensed blood glucose value over a recent series of the plurality of measurements, and wherein the trend indicator comprises a plurality of graphical segments, each of the graphical segments being of different graphical style and assigned to a different range of sensed blood glucose values, thereby indicating a transition from a first range of sensed blood glucose values to a second range of sensed blood glucose values.

According to another aspect of the invention, a method for operating a device for determining blood glucose characteristics is provided, the method comprising steps of receiving a signal from a sensor by a sensor input, the signal being based on a sensed blood glucose value of a user, storing a plurality of measurements of the sensed blood glucose value of the user from the received signal from the sensor in a memory, presenting a graphical representation of the plurality of measurements of the blood glucose characteristic value on a display, and controlling the presentation of the graphical representation on the display by a controller, wherein the step of presenting the graphical representation further comprises a step of presenting a trend indicator indicating an approximate value trend in the sensed blood glucose value over a recent series of the plurality of measurements, the trend indicator comprising a plurality of graphical segments, each of the graphical segments being of different graphical style and assigned to a different range of sensed blood glucose values, thereby for sensed blood glucose value indicating a transition from a first range of sensed blood glucose values to a second range of sensed blood glucose values.

With the help of the invention, the proper operation of the device for determining blood glucose characteristics is improved. The possibility has been provided for the user not only to be able to find out the blood glucose value itself but also to be informed about the trend of the value over time which is derived from the comparison of at least two blood glucose measurements. Depending on whether a rise or a drop or a stability of the blood glucose value is determined, this is shown on the display with the help of the trend indicator. The graphical trend indicator enables the user to quickly comprehend a situation regarding his blood glucose level.

By the invention, it is possible, for example in the scope of discontinuous blood glucose measurements, to provide the patient and/or medical staff information as to the time-related changes of the measured blood glucose values. The time-related changes can show an increase or rise, decrease or drop or constant level of blood glucose values. The information about the time-related changes, namely the trend of blood glucose values, can be determined in the form of a positive or negative slope which corresponds to an increase or decrease. If no time-related change in the blood glucose levels is determined, there is no slope.

The trend indicator is comprised of a plurality of graphical segments which differ in respect of the graphical style used for the display. The differing graphical segments are allocated or assigned to different ranges of sensed blood glucose values. Such a range can cover several possible measurement values or just one. Due to the fact that the trend indicator is comprised of a plurality of different graphical segments, one or more transitions between different ranges of sensed blood glucose values can thus be displayed. If, for example, the trend indicator comprises two graphical segments, the trend indicator will, on the one hand show the trend, namely a rise or drop, for example through variation in the slope of the graphical element. Furthermore, with the help of the graphical segments, which are displayed with differing graphic styles, information is also displayed as to the two ranges between which the transition has occurred. For example, it can be provided that a first graphical segment which relates to a blood glucose value between about 4.0 and about 5.5 mmol/L is displayed in a first color in the trend indicator. If a later measurement value reveals that this value now lies in another range, for example between about 5.5 mmol/L and about 7 mmol/L, the trend indicator with be shown with a graphical segment in a second color. In this example, the trend indicator shows, on the one hand, a rise, for example with the help of an appropriate arrowhead. In addition, the user can see at a glance between which two ranges the transition occurred as a result of the rise.

According to an embodiment, different graphical styles are selected for the graphical segments from the following group of graphic styles: color style and shading style. It can also be provided that two graphical segments differ both in color style and shading style.

In a further embodiment, the controller is configured to perform a time analysis for determining a measurement time for an early measurement providing a first sensed blood glucose value assigned to the first range of sensed blood glucose values and a later measurement providing a second sensed blood glucose value assigned to the second range of sensed blood glucose values, and prevent the graphical representation of the trend indicator on the display if from the time analysis one of the following conditions is concluded: a time interval between the early and the later measurement is shorter than a minimum time interval, and the time interval between the early and the later measurement is longer than a maximum time interval. In this embodiment it is also provided that, in addition to the trend analysis, the time interval between the measurements can be analyzed in order to determine the blood glucose values from which the graphically displayed trend indicator was derived. The representation of the trend indicator is prevented by the controller if the time interval is shorter than a particular minimum length. The representation of the trend indicator is also prevented if the time interval is too long. The values for the minimum and maximum time interval can be set by the user or predefined by the device. In this way, a trend display is prevented in situations where a trend cannot be determined properly for the respective blood glucose values due to a too long or too short interval between the measurements.

According to another embodiment, the trend indicator indicates a trend mode for the sensed blood glucose values selected from the following group: moderate drop, moderate rise, steep drop, and steep rise. The differentiation between steep and moderate can be realized, for example through the trend indicator being displayed as a vertical or diagonal arrow whereby a vertical arrow would show a steep change either a rise or a drop.

In yet another embodiment, a device integrated sensor is provided. In this embodiment the device is provided with the sensor itself. Different configurations of devices for determining blood glucose characteristics based on a test element analysis are known, e.g. from US 2007/0293790 A1.

In still another embodiment, the graphical representation comprises a warning symbol indicating that a recent blood glucose value of the sensed blood glucose value belongs to a risk situation. A risk situation may be determined by the controller by evaluating at least one of the following: sensed blood glucose value(s), trend of the blood glucose values, extrapolation for future blood glucose value, time interval information for measurements of the blood glucose value, day time information and injected bolus information.

With respect to the method for operating a device for determining blood glucose characteristics, preferred embodiments may be provided as described in detail for the device above.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
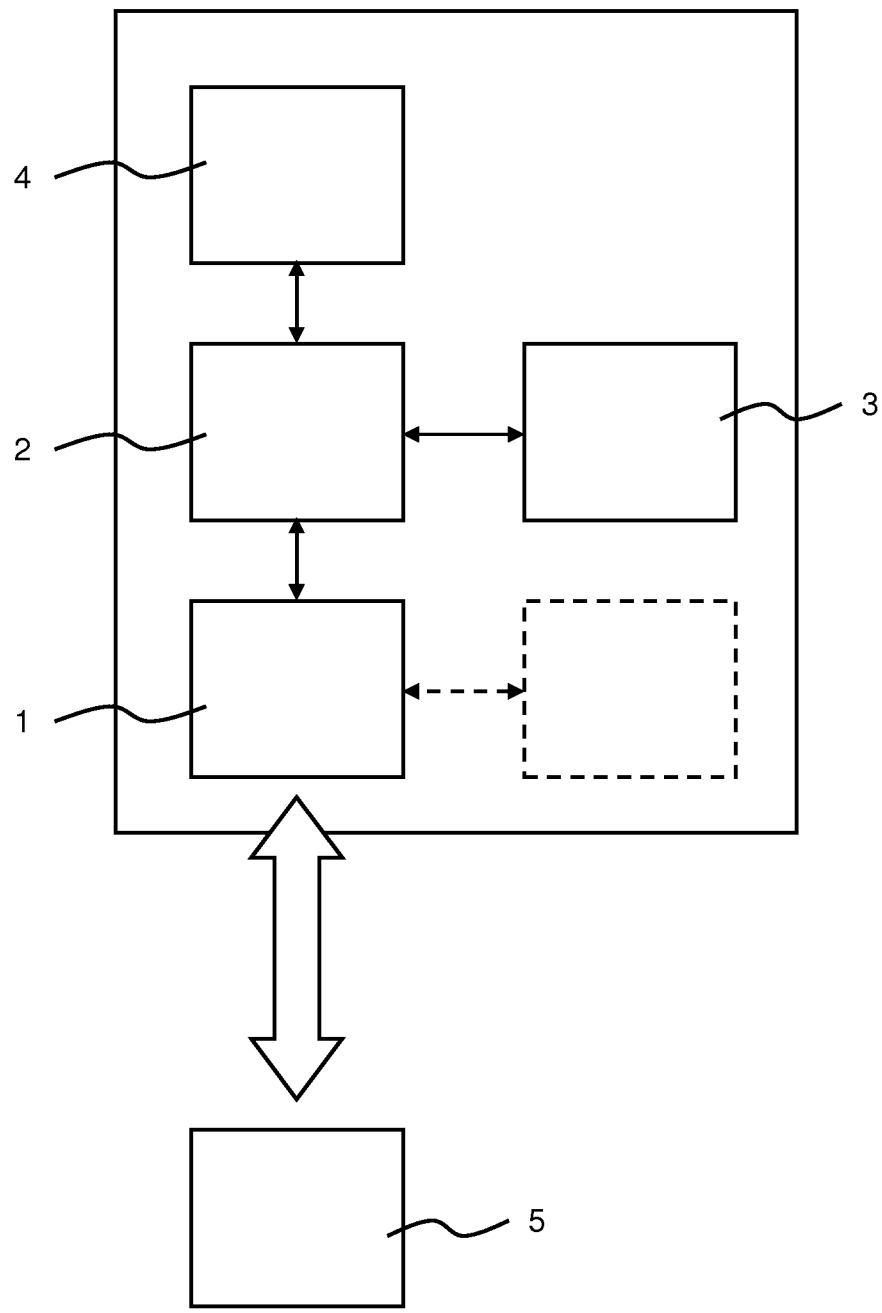
FIG. 1 is a schematic representation of device for determining blood glucose characteristics.

FIG. 1 shows a schematic representation of a device for determining blood glucose value characteristics with a sensor input 1, a controller 2 and a memory 3. The controller 2 is connected to a display 4 in order to control the representation of the graphical elements on the display 4. In the case of the embodiment shown in FIG. 1, a sensor 5 is shown as an external sensor configured to measure blood glucose value characteristics for a user. One possible method for sensing blood glucose values is a discontinuous mode. In another embodiment, the sensor 5 can be integrated into the device, represented in FIG. 1 as a dashed line. For example, this would then by a device for determining blood glucose with the help of so-called test strips, whereby a blood sample is applied to the test strips in order to determine the blood glucose value.

The signals sensed by the sensor 5 to the sensor input 1 on the respective blood glucose value characteristics, are then processed by the controller 2 in order to generate controlling signals for the display 4, in particular to display graphical elements which represent the blood glucose values and/or information pertaining to changes per time unit (trend).

Figure 2:
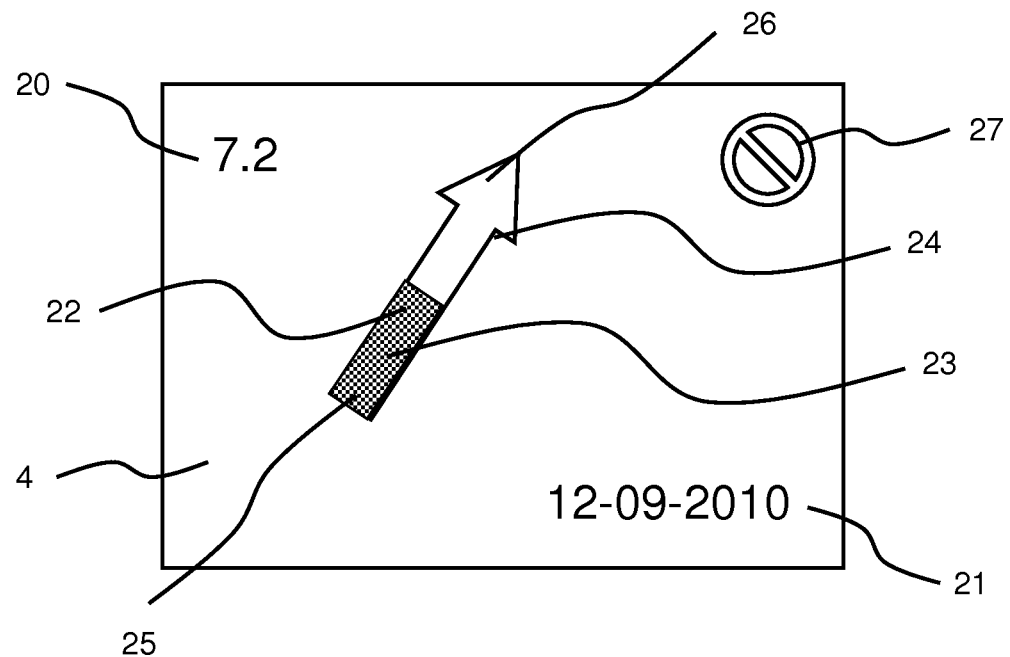
FIG. 2 is a schematic representation of presentations on a display of the device in FIG. 1.
Figure 2:
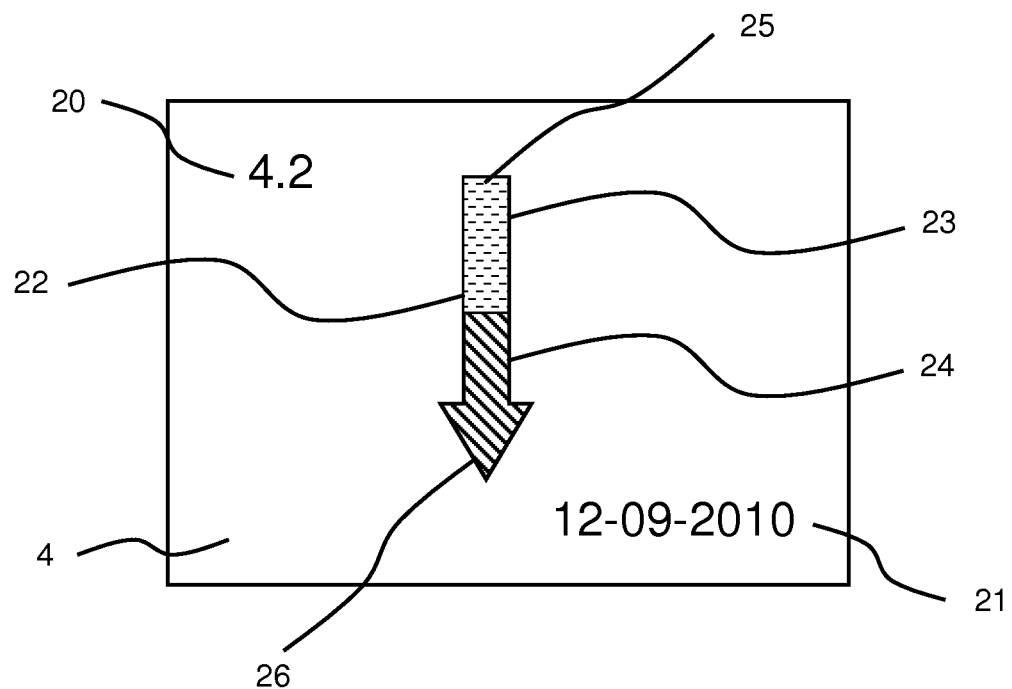

FIG. 2 shows a schematic representation of presentations to be shown on the display 4. In the embodiment shown, the display 4 shows a present blood glucose value 20 as well as date information 21. Furthermore, a trend indicator 22 is shown which, in the embodiment shown, has the form of an arrow. The trend indicator 22 comprises, in each of the two representations in FIG. 2, two different graphical segments 23, 24 which differ in terms of the shading used.

The first graphical segment 23 shows, through means of its graphical style, that the starting point selected for the trend analysis was in an initial range of blood glucose values, for example in a range between about 3.5 mmol/L and about 5 mmol/L. The later value for the trend analysis, in the upper representation in FIG. 2, lies in another range of blood glucose values which is expressed in the second graphical segment 24 by way of the lack of shading. For example, the range here may cover blood glucose values between about 6 mmol/L and about 8 mmol/L. The slope of the arrow displayed in the upper representation in FIG. 2 indicates a moderate rise in the blood glucose value in the time period analyzed.

In contrast, the trend indicator 22 in the lower representation in FIG. 2, shows a steep drop derived from the blood glucose values measured for the trend analysis. In the lower representation in FIG. 2, the graphical segments 23, 24 also differ in respect of their shading and thus show that the steep drop led to a transition from one range of blood glucose values to another range of blood glucose values.

The graphical segment at the arrowhead 25 shows with its graphical style the range in which the previous blood glucose value used for the trend analysis has fallen. The graphical segment at the arrowhead 26 of the trend indicator 22 shows, by means of its graphical style, the range into which the blood glucose values of the later blood glucose value used for the trend analysis has fallen.

It can also be provided that the trend indicator 22 comprises more than two different graphical segments which differ in terms of their graphic style.

Referring to FIG. 1, a warning symbol 27 is presented on the display 4. The warning indicates that the present blood glucose value is in a critical range of blood glucose values. The controller 2 will generate control signals for displaying the warning symbol 27 depending on predefined rules which may be adapted by the user. In one embodiment, the following exemplary rules may be applied:

measured blood glucose value is <about 60 mg/dl;

measured blood glucose value is >about 300 mg/dl;

measured blood glucose value was taken after main meal AND previous blood glucose value was before main meal AND extrapolated blood glucose value in about 2 hours is <about 90 mg/dl OR extrapolated blood glucose value in about 2 hours is >about 300 mg/dl;

measured blood glucose value was taken before main meal AND previous blood glucose value was taken after main meal AND extrapolated blood glucose value in about 1 hour is <about 60 mg/dl OR extrapolated blood glucose value in about 1 hour is >about 250 mg/dl;

none of the above mentioned information about meal relation AND extrapolated blood glucose value in about 2 hours is <about 60 mg/dl OR extrapolated blood glucose value in about two hours is >about 300 mg/dl;

measured blood glucose value is <about 60 mg/dl AND blood glucose value was <about 60 mg/dl at same time on the previous day (time interval between about 23 hours and about 25 hours);

measured blood glucose value is >about 100 mg/dl AND hypo symptoms are entered;

measured blood glucose value is <about 50 mg/dl AND no hypo symptoms are set; or measured blood glucose value is outside (below/above) a target range AND the same blood glucose value trend happened the day before (same blood glucose value–blood glucose value difference ≤about 20 mg/dl AND difference in slopes ≤±about 9 mg/dl*h AND difference in time of day ≤±about 1 hour AND both values taken before or after main meal).

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A device for determining blood glucose characteristics, comprising:
    a sensor input configured for receiving a signal from a sensor, the signal being based on a sensed blood glucose value of a user;
    a memory configured for storing a plurality of measurements of the sensed blood glucose value of the user from the received signal from the sensor;
    a display configured for presenting a graphical representation of the plurality of measurements of the sensed blood glucose value; and
    a controller configured for controlling the presentation of the graphical representation on the display,
    wherein the graphical representation comprises a trend indicator adapted to indicate an approximate value trend in the sensed blood glucose value over a recent series of the plurality of measurements, wherein the trend indicator comprises a plurality of graphical segments, each of the graphical segments being of different graphical style and assigned to a different range of sensed blood glucose values, each segment being configured for indicating a transition from a first range of sensed blood glucose values to a second range of sensed blood glucose values, and wherein the trend indicator further comprises a slope for indicating a rate of change of the transition from the first range of sensed blood glucose values to the second range of sensed blood glucose values, and
    wherein the controller is further configured to perform a time analysis for determining a measurement time for an early measurement providing a first sensed blood glucose value assigned to the first range of sensed blood glucose values and a later measurement providing a second sensed blood glucose value assigned to the second range of sensed blood glucose values, and wherein the controller is further configured to prevent the graphical representation of the trend indicator on the display if from the time analysis one of the following conditions is concluded: a time interval between the early and the later measurement is shorter than a minimum time interval, and the time interval between the early and the later measurement is longer than a maximum time interval.

2. The device according to claim 1, wherein the graphical segments are selectable based on different graphical styles selected from the group of graphic styles consisting of color style and shading style.

3. The device according to claim 1, wherein the slope of the trend indicator is configured for indicating a trend mode for the sensed blood glucose values selected from the following group of trends: moderate drop, moderate rise, steep drop, and steep rise.

4. The device according to claim 1, wherein the sensor comprises a device integrated sensor.

5. The device according to claim 4, wherein the device integrated sensor is configured to sense the blood glucose values from a test element analysis.

6. The device according to claim 1, wherein the signals received by the sensor input comprise sensed blood glucose values from a discontinuous mode of blood glucose measurement.

7. The device according to claim 1, wherein the graphical representation comprises a warning symbol indicating that a recent blood glucose value of the sensed blood glucose value belongs to a risk situation.

8. The device of claim 1, wherein the trend indicator has two graphical segments.

* * * * *